United States Patent [19]

Gallant et al.

[11] Patent Number: 5,532,237
[45] Date of Patent: Jul. 2, 1996

[54] INDOLE DERIVATIVES WITH AFFINITY FOR THE CANNABINOID RECEPTOR

[75] Inventors: Michel Gallant, Montreal; Yves Gareau, Quebec; Daniel Guay, Quebec; Marc Labelle, Quebec; Petpiboon Prasit, Quebec, all of Canada

[73] Assignee: Merck Frosst Canada, Inc., Kirkland, Canada

[21] Appl. No.: 388,929

[22] Filed: Feb. 15, 1995

[51] Int. Cl.[6] .................. A61K 31/40; A61K 31/535; C07D 209/14; C07D 413/06

[52] U.S. Cl. .................. 514/235.2; 514/414; 514/415; 544/58.5; 544/143; 544/144; 544/373; 546/201; 548/483; 548/468; 548/504; 548/506

[58] Field of Search .................. 548/504; 544/143; 514/235.2

[56] References Cited

U.S. PATENT DOCUMENTS

| | | |
|---|---|---|
| 3,161,654 | 12/1964 | Shen et al. . |
| 3,489,770 | 1/1970 | Herbst . |
| 3,501,465 | 3/1970 | Shen et al. .................. 548/504 |
| 4,021,431 | 5/1977 | Zenitz .................. 548/504 |
| 4,973,587 | 11/1990 | Ward et al. . |
| 5,013,837 | 5/1991 | Ward et al. . |
| 5,081,122 | 1/1992 | Ward . |

FOREIGN PATENT DOCUMENTS

| | | |
|---|---|---|
| 0444451A2 | 4/1991 | European Pat. Off. . |
| 2692575A1 | 12/1993 | France . |
| 1374414 | 1/1974 | United Kingdom . |

OTHER PUBLICATIONS

Matsuda, L. et al., Nature 1990, 346 pp. 561–564.
Munro, S. et al., Nature 1993, 365; pp. 61–65.
Razdan, R. K. Pharmacol. Rev. 1986, 38; pp. 75–149.
D'Ambra, T. E. et al., Jo Med. Chem. 1992, 35; pp. 124–135.
Bell, M. R. et al., J. Med Chem. 1991, 34: pp. 1099–1100.
Devane, W. A. et al, Science, 1992, 258; pp. 1946–1949.
Hollister, L. E. Pharmacol. Rev. 1986, 38; pp. 1–20.

*Primary Examiner*—Robert W. Ramsuer
*Attorney, Agent, or Firm*—Sylvia A. Ayler; Mark R. Daniel

[57] ABSTRACT

Disclosed are indole derivatives having activity on the cannabinoid receptors and the methods of their preparation. The compounds are useful for lowering ocular intra ocular pressure and treating glaucoma because of the activity on the cannabinoid receptor.

5 Claims, No Drawings

INDOLE DERIVATIVES WITH AFFINITY FOR THE CANNABINOID RECEPTOR

BACKGROUND OF THE INVENTION

The terms cannabinoid or cannabimimetic compound apply to compounds which produce a physiological effect similar to that of the plant Cannabis Sativa, or a compound that has affinity for the cannabinoid receptors $CB_1$ or $CB_2$. See Matsuda, L.; Lolait, S. J.; Brownstein, M. J.; Young, A. C.; Bonner, T. I. Structure of a cannabinoid receptor and functional expression of the cloned cDNA. Nature, 1990, 346, 561–564: Munro, S.; Thomas, K. L.; Abu-Shaar, M. Molecular characterization of the peripheral receptor of cannabinoids. Nature, 1993, 1993, 61–65. Examples of such compounds are $\Delta^9$-THC and its analogs (Razdan, R. K. Structure activity relationship in the cannabinoids. Pharmacol. Rev., 1986, 38, 75–149), WIN-55212-2 and its analogs (D'Ambra, T. E.; Estep, K. G.; Bell, M. R.; Eissenstat, M. A.; Josef, K. A.; Ward, S. J.; Haycock, D. A.; Baizman, E. R.; Casiano, F. M.; Beglin, N. C.; Chippad, S. M.; Grego, J. D.; Kullnig, R. K.; Daley, G. T. Conformationnaly restrained analogues of Pravadoline: Nanomolar potent, enantioselective, aminoalkylindole agonist of the cannabinoid receptor. J. Med. Chem., 1992, 35, 124–135: Bell, M. R.; D'Ambra, T. E.; Kumar, V.; Eissenstat, M. A.; Hermann, J. L.; Wetzel, J. R.; Rosi, D.; Philion, R. E.; Daum, S. J.; Hlasta, D. J.; Kullnig, R. K.; Ackerman, J. H.; Haubrich, D. R.; Luttinger, D. A.; Baizman, E. R.; Miller, M. S.; Ward, S. J. Antinociceptive aminoalkylindoles. J. Med. Chem., 1991, 34, 1099–1100), CP-55940 and its analogs (Johnson, M. R.; Melvin, L. S. The discovery of non-classical cannabinoid analgetics. In "Cannabinoids as therapeutic agents", 1986, Mechoulam, R., Ed., CRC Press: Boca Raton Fla., pp.121–145), SR141716A and its analogs (Barth, F.; Casellas, P.; Congy, C.; Martinez, S.; Rinaldi, M. Nouveaux derives du pyrazole, procede pour leur preparation et composition pharmaceutiques les contenant. French Patent 2692575-A1, 1992: Barth, F.; Heaulme, M.; Shire, D.; Calandra, B.; Congy, C.; Martinez, S.; Maruani, J.; Neliat, G.; Caput, D.; Ferrara, P.; Soubrie, P.; Breliere, J-C.; Le Fur, G.; Rinaldi-Carmona, M. SR141716A, a potent and selective antagonist of the brain cannabinoid receptor. International Cannabis Research Society Conference Abstract, July 1994, L'Estèrel, Canada, p. 33), and anandamide (Devane, W. A.; Hanus, L.; Breuer, A.; Pertwee, R. G.; Stevenson, L. A.; Griffin, G.; Gibson, D.; Mandelbaum, A.; Etinger, A.; Mechoulam, R. Isolation and structure of a brain constituent that binds to the cannabinoid receptor. Science, 1992, 258, 1946–1949) and its analogs. Anandamide has been termed the endogenous ligand of the $CB_1$ receptor, as it is synthesized near its site of action and is potent and selective for the $CB_1$ receptor.

The biological activity of cannabinoids has been extensively reviewed. See Hollister, L. E. Health aspects of Cannabis. Pharmacol. Rev., 1986, 38, 1–20. Their usefulness in various disease states has been discussed. See The therapeutic potential of marihuana. Cohen, S. and Stillman, R. C., eds. Plenum: New York, 1976.

Additionally, U.S. Pat. Nos. 4,973,587 and 5,013,837 (Ward et al.) disclose compounds of formula 1:

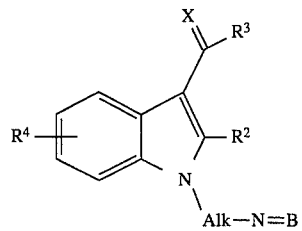

having antiglaucoma compositions where:

$R_2$ is hydrogen, lower alkyl, chloro or fluoro;

$R_3$ is phenyl ( or phenyl substituted by from one to three substituents selected from halogen, lower alkoxy, lower alkoxymethyl, hydroxy, lower alkyl, amino, lower alkylamino, di-lower alkylamino or lower alkylmercapto), methylenedioxyphenyl, benzyl, styryl, lower alkoxystyryl, 1- or 2-naphthyl,) or 1- or 2-naphthyl substituted by from one to two substituents selected from lower alkyl, lower alkoxy, halo or cyano), (1H-imidazol-1-yl)naphthyl, 2-(1-naphthyl)ethenyl, 1-(1,2,3,4-tetrahydronaphthyl),anthryl, phenanthryl, pyrenyl, 2-, 3-, 4-, 5-, 6- or 7-benzo[b]furyl, 2or 3-benzo[b]thienyl, 5-(1H-benzimidazolyl) or 2-, 3-, 4-, 5-, 6-, 7- or 8-quinolyl;

$R_4$ is hydrogen or lower alkyl, hydroxy, lower alkoxy or halo in the 4-, 5-, 6- or 7-positions;

X is O or S;

Alk is lower alkylene having the formula $(CH_2)_n$ where n is the integer 2 or 3, or such lower-alkylene substituted by a lower-alkyl group; and N=B is N,N-di-lower alkylamino, 4-morpholinyl, 2-lower alkyl- 4-morpholinyl, 3-lower alkylmorpholinyl, 1-pyrrolidinyl, 1-piperidinyl or 3-hydroxy-1-piperidinyl.

U.S. Pat. No. 5,081,122 (Ward) discloses compounds of formula 2:

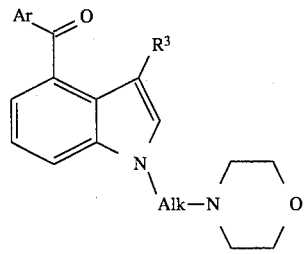

having antiglaucoma compositions where:

Ar is lower alkoxyphenyl or 1- or 2-naphthyl;

$R_3$ is hydrogen or lower alkyl;

Alk is lower alkylene containing from two to four carbon atoms.

The present compounds differ from Ward's (formula 1 and 2) primarily in having a carbonyl on the nitrogen of the indole while it is at the 4-position in the case of the U.S. Pat. No. 5,081,122.

EP 0 444 451 generically discloses a compound of formula

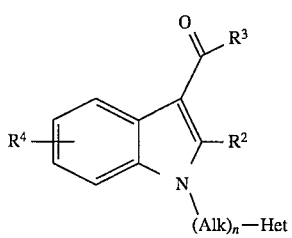

useful as analgesic, anti-rheumatic, anti-inflammatory or anti-glaucoma agents where:

$R_2$ is hydrogen, lower alkyl;

$R_3$ is phenyl ( or phenyl substituted by from one to three substituents selected from halogen, lower alkoxy, hydroxy, lower alkyl, nitro, amino, lower alkylamino, di-lower alkylamino, loweralkylmercapto, lower alkylsulfinyl, lower alkylsulfonyl and methylenedioxy), 2- or 4-biphenyl or 1- or 2-naphthyl (or 1- or 2-naphthyl substituted by from one to two substituents selected from lower alkyl, lower alkoxy, halogen, lower alkylmercapto, lower alkylsulfinyl, lower alkylsulfonyl and trifluoromethyl);

$R_4$ is hydrogen or from one to two substituents selected from loweralkyl, hydroxy, lower alkoxy, and halogen at the 4-, 5-, 6- or 7- positions;

Alk is lower alkylene containing from two to four carbon atoms which may contain a lower alkyl group;

n is 0 or 1;

Het is an aliphatic heterocycle, 2-piperazinyl and 2-indolinyl.

The present compound differs from formula 3 primarily in having a carbonyl on the nitrogen of the indole.

U.S. Pat. No. 3,489,770 generically discloses compound having the following formula 4:

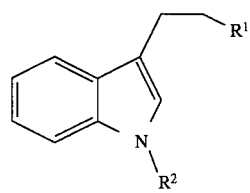

The compounds are said to have anti-inflammatory, hypotensive, hypoglycemic and CNS activities. Although not within the ambit of the above-defined genus, the patent also discloses a variety of species where $R_2$ is an arylcarbonyl group.

British Patent 1,374,414 and U.S. Pat. No. 4,021,431 generically discloses compounds having the following structural formula 5:

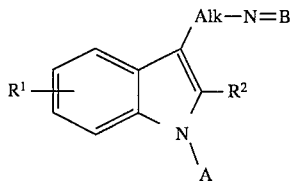

The compounds are useful as anti-inflammatory agents. Although not within the ambit of the above-defined genus, the patent also discloses a variety of species where A is an arylcarbonyl group.

SUMMARY OF THE INVENTION

The present invention relates to indoles having activity on the cannabinoid receptor CB2 and the methods of their preparation.

Because of this activity on the cannabinoid receptor, the compounds of the present invention are useful for lowering the IOP (intra ocular pressure).

DETAIL DESCRIPTION OF THE INVENTION

The compounds of the invention can be summarized by formula I:

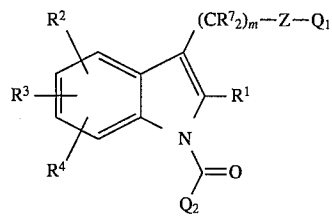

wherein:

$R^1$ is H, lower alkyl, aryl, benzyl, or lower fluorinated alkyl;

$R^{2-4}$ is independently, H, lower alkyl, lower fluorinated alkyl, halogen, $NO_2$, CN, $—(CR^7_2)_m—OR^1$, $—(CR^7_2)_m— S(O)nR^6_2$, or $—(CR^7_2)m—R^6$;

$R^5$ is H, lower alkyl, aryl, or benzyl;

$R^6$ is lower alkyl, aryl, benzyl, or $N(R^5)_2$;

$R^7$ is H, or lower alkyl; $R^8$ is $R^7$, lower fluorinated alkyl, halogen, $OR^{7,}$ or lower alkyl thio;

$R^9$ is $R^7$, lower fluorinated alkyl, halogen, $OR^7$, or lower alkyl thio;

$Q_1$ is H, $OR^7$, CHO, CN, $CO_2R^7$, $C(O)SR^7$, $S(O)_nR^6$, HET or $N(R^7)_2$, wherein two $R^7$ groups may be joined to form a pyrrolidine, piperidine, piperazine, morpholine or thiomorpholine ring and their quaternary methyl ammonium salts;

$Q_2$ is phenyl, naphthyl, quinolinyl, furanyl, thienyl, pyridinyl, anthracyl, benzothienyl, benzofuranyl or thieno[3,2-b]-pyridinyl, mono-, di- or trisubstituted with $R^8$;

HET is is a diradical of benzene, thiazole, thiophene, or furan, substituted with one or two $R^9$ groups;

Z is CO or a bond.

m is 0–6; and n is 0,1, or 2.

Definitions

| The following abbreviations have the indicated meanings: | |
|---|---|
| DCC = | 1,3-dicyclohexylcarbodiimide |
| DIBAL = | diisobutyl aluminum hydride |
| DMAP = | 4-(dimethylamino)pyridine |
| DMF = | N,N-dimethylformamide |
| DMSO = | dimethyl sulfoxide |
| HMPA = | hexamethylphosphoramide |
| KHMDS = | potassium hexamethyldisilazane |
| LDA = | lithium diisopropylamide |
| MCPBA = | metachloroperbenzoic acid |
| Ms = | methanesulfonyl = mesyl |
| MsO = | methanesulfonate = mesylate |
| NBS = | N-bromosuccinimide |
| PCC = | pyridinium chlorochromate |
| PDC = | pyridinium dichromate |
| Ph = | phenyl |

The following abbreviations have the indicated meanings:

| | |
|---|---|
| PPTS = | pyridinium p-toluene sulfonate |
| pTSA = | p-toluene sulfonic acid |
| Pye = | pyridinediyl |
| r.t. = | room temperature |
| rac. = | racemic |
| Tf = | trifluoromethanesulfonyl = triflyl |
| TfO = | trifluoromethanesulfonate = triflate |
| THF = | tetrahydrofuran |
| THP = | tetrahydropyran-2-yl |
| TLC = | thin layer chromatography |
| Ts = | p-toluenesulfonyl = tosyl |
| TsO = | p-toluenesulfonate = tosylate |
| Tz = | 1H (or 2H)-tetrazol-5-yl |
| $SO_2$ = | =O=S=O |
| Alkyl group abbreviations | |
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |

The term alkyl means linear, branched, and cyclic structures and combinations thereof.

"Lower alkyl" means alkyl groups of from 1 to 7 carbon atoms. Examples of lower alkyl groups include methyl, ethyl, propyl, isopropyl, s- and t-butyl, pentyl, hexyl, heptyl, cyclopropyl, cyclohexylmethyl, and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched, or cyclic configuration. Examples of lower alkylthio groups include methylthio, propylthio, isopropylthio, cycloheptylthio, etc. By way of illustration, the propylthio group signifies —$SCH_2CH_2CH_3$.

"Aryl" includes phenyl and phenyl monosubstituted by halogen, a lower alkoxy or a lower alkylthio group.

"Lower fluorinated alkyl" means alkyl groups of from 1 to 7 carbon atoms in which one or more of the hydrogen atoms has been replaced by fluorine.

"Benzyl" includes mono or disubstitution on the aromatic ring by halogen, lower alkoxy or lower alkylthio groups. The hydrogens of the methylene moiety could be replace by lower alkyl.

Halogen includes F, Cl Br, and I.

It is intended that the definition of any substituent (e.g., $R^5$) in a particular molecule be independent of its definition elsewhere in the molecule. Thus,—$N(R^5)_2$ represents —NHH,—$NHCH_3$, —$NHC_6H_5$, etc.

Optical Isomers—Diastereomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, is benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Examples of the novel compounds of this invention are as follows:

TABLE 1

| CPD | $R^1$ | $R^2$ | $R^3$ | $R^4$ | $R^{7*}$ | Z | $Q_1$ | $Q_2$ |
|---|---|---|---|---|---|---|---|---|
| 1 | $CH_3$ | H | H | Cl | H | — | 4-MORPHOLINE | 2-CHLOROPHENYL |
| 2 | $CH_3$ | H | H | F | H | — | 4-MORPHOLINE | 2-CHLOROPHENYL |
| 3 | $CH_3$ | H | H | Br | H | — | 4-MORPHOLINE | 2-CHLOROPHENYL |
| 4 | $CH_3$ | H | H | $OCH_3$ | H | — | 4-MORPHOLINE | 2-CHLOROPHENYL |
| 5 | $CH_3$ | H | H | $CF_3$ | H | — | 4-MORPHOLINE | 2-CHLOROPHENYL |
| 6 | $CH_3$ | H | H | $C_2F_5$ | H | — | 4-MORPHOLINE | 2-CHLOROPHENYL |
| 7 | $CH_3$ | H | H | $NO_2$ | H | — | 4-MORPHOLINE | 2-CHLOROPHENYL |
| 8 | $CH_3$ | H | H | Ph | H | — | 4-MORPHOLINE | 2-CHLOROPHENYL |
| 9 | $CH_3$ | H | H | $NH_2$ | H | — | 4-MORPHOLINE | 2-CHLOROPHENYL |

TABLE 1-continued

| CPD | R$^1$ | R$^2$ | R$^3$ | R$^4$ | R$^{7*}$ | Z | Q$_1$ | Q$_2$ |
|---|---|---|---|---|---|---|---|---|
| 10 | CH$_3$ | H | H | N(CH$_3$)$_2$ | H | — | 4-MORPHOLINE | 2-CHLOROPHENYL |
| 11 | CH$_3$ | H | H | N(Bn)$_2$ | H | — | 4-MORPHOLINE | 2-CHLOROPHENYL |
| 12 | CH$_3$ | H | H | N(Ph)$_2$ | H | — | 4-MORPHOLINE | 2-CHLOROPHENYL |
| 13 | CH$_3$ | H | H | CN | H | — | 4-MORPHOLINE | 2-CHLOROPHENYL |
| 14 | CH$_3$ | H | H | SO$_2$CH$_3$ | H | — | 4-MORPHOLINE | 2-CHLOROPHENYL |
| 15 | CH$_3$ | H | H | SO$_2$Ph | H | — | 4-MORPHOLINE | 2-CHLOROPHENYL |
| 16 | CH$_3$ | H | H | SO$_2$NH$_2$ | H | — | 4-MORPHOLINE | 2-CHLOROPHENYL |
| 17 | CH$_3$ | H | H | SO$_2$NHCH$_3$ | H | — | 4-MORPHOLINE | 2-CHLOROPHENYL |
| 18 | CH$_3$ | H | H | SO$_2$N(CH$_3$)$_2$ | H | — | 4-MORPHOLINE | 2-CHLOROPHENYL |
| 19 | CH$_3$ | H | H | CH$_3$ | H | — | 4-MORPHOLINE | 2-CHLOROPHENYL |
| 20 | CH$_3$ | H | H | C$_2$H$_5$ | H | — | 4-MORPHOLINE | 2-CHLOROPHENYL |
| 21 | CH$_3$ | H | H | n-C$_3$H$_7$ | H | — | 4-MORPHOLINE | 2-CHLOROPHENYL |
| 22 | CH$_3$ | H | H | OH | H | — | 4-MORPHOLINE | 2-CHLOROPHENYL |
| 23 | CH$_3$ | H | H | OC$_2$H$_5$ | H | — | 4-MORPHOLINE | 2-CHLOROPHENYL |
| 24 | CH$_3$ | H | H | OC$_3$H$_7$ | H | — | 4-MORPHOLINE | 2-CHLOROPHENYL |
| 25 | CH$_3$ | H | H | OPh | H | — | 4-MORPHOLINE | 2-CHLOROPHENYL |
| 26 | CH$_3$ | H | H | OBn | H | — | 4-MORPHOLINE | 2-CHLOROPHENYL |
| 27 | CH$_3$ | H | H | OCF$_3$ | H | — | 4-MORPHOLINE | 2-CHLOROPHENYL |
| 28 | CH$_3$ | H | H | Cl | H | CO | 4-MORPHOLINE | 2-CHLOROPHENYL |
| 29 | CH$_3$ | H | H | F | H | CO | 4-MORPHOLINE | 2-CHLOROPHENYL |
| 30 | CH$_3$ | H | H | Br | H | CO | 4-MORPHOLINE | 2-CHLOROPHENYL |
| 31 | CH$_3$ | H | H | OCH$_3$ | H | CO | 4-MORPHOLINE | 2-CHLOROPHENYL |
| 32 | CH$_3$ | H | H | CF$_3$ | H | CO | 4-MORPHOLINE | 2-CHLOROPHENYL |
| 33 | CH$_3$ | H | H | C$_2$F$_5$ | H | CO | 4-MORPHOLINE | 2-CHLOROPHENYL |
| 34 | CH$_3$ | H | H | NO$_2$ | H | CO | 4-MORPHOLINE | 2-CHLOROPHENYL |
| 35 | CH$_3$ | H | H | Ph | H | CO | 4-MORPHOLINE | 2-CHLOROPHENYL |
| 36 | CH$_3$ | H | H | NH$_2$ | H | CO | 4-MORPHOLINE | 2-CHLOROPHENYL |
| 37 | CH$_3$ | H | H | N(CH$_3$)$_2$ | H | CO | 4-MORPHOLINE | 2-CHLOROPHENYL |
| 38 | CH$_3$ | H | H | N(Bn)$_2$ | H | CO | 4-MORPHOLINE | 2-CHLOROPHENYL |
| 39 | CH$_3$ | H | H | N(Ph)$_2$ | H | CO | 4-MORPHOLINE | 2-CHLOROPHENYL |
| 40 | CH$_3$ | H | H | CN | H | CO | 4-MORPHOLINE | 2-CHLOROPHENYL |
| 41 | CH$_3$ | H | H | SO$_2$CH$_3$ | H | CO | 4-MORPHOLINE | 2-CHLOROPHENYL |
| 42 | CH$_3$ | H | H | SO$_2$Ph | H | CO | 4-MORPHOLINE | 2-CHLOROPHENYL |
| 43 | CH$_3$ | H | H | SO$_2$NH$_2$ | H | CO | 4-MORPHOLINE | 2-CHLOROPHENYL |
| 44 | CH$_3$ | H | H | SO$_2$NHCH$_3$ | H | CO | 4-MORPHOLINE | 2-CHLOROPHENYL |
| 45 | CH$_3$ | H | H | SO$_2$NCH$_3$)$_2$ | H | CO | 4-MORPHOLINE | 2-CHLOROPHENYL |
| 46 | CH$_3$ | H | H | CH$_3$ | H | CO | 4-MORPHOLINE | 2-CHLOROPHENYL |
| 47 | CH$_3$ | H | H | C$_2$H$_5$ | H | CO | 4-MORPHOLINE | 2-CHLOROPHENYL |
| 48 | CH$_3$ | H | H | n-C$_3$H$_7$ | H | CO | 4-MORPHOLINE | 2-CHLOROPHENYL |
| 49 | CH$_3$ | H | H | OH | H | CO | 4-MORPHOLINE | 2-CHLOROPHENYL |
| 50 | CH$_3$ | H | H | OC$_2$H$_5$ | H | CO | 4-MORPHOLINE | 2-CHLOROPHENYL |
| 51 | CH$_3$ | H | H | OC$_3$H$_7$ | H | CO | 4-MORPHOLINE | 2-CHLOROPHENYL |
| 52 | CH$_3$ | H | H | OPh | H | CO | 4-MORPHOLINE | 2-CHLOROPHENYL |
| 53 | CH$_3$ | H | H | OBn | H | CO | 4-MORPHOLINE | 2-CHLOROPHENYL |
| 54 | CH$_3$ | H | H | OCF$_3$ | H | CO | 4-MORPHOLINE | 2-CHLOROPHENYL |
| 55 | CH$_3$ | H | H | H | H | — | 4-MORPHOLINE | 2,3-DICHLOROPHENYL |
| 56 | CH$_3$ | H | H | F | H | — | 4-MORPHOLINE | 2,3-DICHLOROPHENYL |
| 57 | CH$_3$ | H | H | Cl | H | — | 4-MORPHOLINE | 2,3-DICHLOROPHENYL |
| 58 | CH$_3$ | H | H | OCH$_3$ | H | — | 4-MORPHOLINE | 2,3-DICHLOROPHENYL |
| 59 | CH$_3$ | H | H | OCF$_3$ | H | — | 4-MORPHOLINE | 2,3-DICHLOROPHENYL |
| 60 | CH$_3$ | H | H | CF$_3$ | H | — | 4-MORPHOLINE | 2,3-DICHLOROPHENYL |
| 61 | CH$_3$ | H | H | SO$_2$CH$_3$ | H | — | 4-MORPHOLINE | 2,3-DICHLOROPHENYL |
| 62 | CH$_3$ | H | H | SO$_2$N(CH$_3$)$_2$ | H | — | 4-MORPHOLINE | 2,3-DICHLOROPHENYL |
| 63 | CH$_3$ | H | H | H | H | — | 4-MORPHOLINE | 1-NAPHTHYL |
| 64 | CH$_3$ | H | H | F | H | — | 4-MORPHOLINE | 1-NAPHTHYL |
| 65 | CH$_3$ | H | H | Cl | H | — | 4-MORPHOLINE | 1-NAPHTHYL |
| 66 | CH$_3$ | H | H | OCH$_3$ | H | — | 4-MORPHOLINE | 1-NAPHTHYL |
| 67 | CH$_3$ | H | H | OCF$_3$ | H | — | 4-MORPHOLINE | 1-NAPHTHYL |
| 68 | CH$_3$ | H | H | CF$_3$ | H | — | 4-MORPHOLINE | 1-NAPHTHYL |
| 69 | CH$_3$ | H | H | SO$_2$CH$_3$ | H | — | 4-MORPHOLINE | 1-NAPHTHYL |
| 70 | CH$_3$ | H | H | SO$_2$N(CH$_3$)$_2$ | H | — | 4-MORPHOLINE | 1-NAPHTHYL |
| 71 | CH$_3$ | H | H | H | H | — | 4-MORPHOLINE | 2-NAPHTHYL |
| 72 | CH$_3$ | H | H | F | H | — | 4-MORPHOLINE | 2-NAPHTHYL |
| 73 | CH$_3$ | H | H | Cl | H | — | 4-MORPHOLINE | 2-NAPHTHYL |
| 74 | CH$_3$ | H | H | OCH$_3$ | H | — | 4-MORPHOLINE | 2-NAPHTHYL |
| 75 | CH$_3$ | H | H | OCF$_3$ | H | — | 4-MORPHOLINE | 2-NAPHTHYL |
| 76 | CH$_3$ | H | H | CF$_3$ | H | — | 4-MORPHOLINE | 2-NAPHTHYL |
| 77 | CH$_3$ | H | H | SO$_2$CH$_3$ | H | — | 4-MORPHOLINE | 2-NAPHTHYL |
| 78 | CH$_3$ | H | H | SO$_2$N(CH$_3$)$_2$ | H | — | 4-MORPHOLINE | 2-NAPHTHYL |
| 79 | CH$_3$ | H | H | H | H | — | 4-MORPHOLINE | 2-THIENYL |
| 80 | CH$_3$ | H | H | F | H | — | 4-MORPHOLINE | 2-THIENYL |
| 81 | CH$_3$ | H | H | Cl | H | — | 4-MORPHOLINE | 2-THIENYL |
| 82 | CH$_3$ | H | H | OCH$_3$ | H | — | 4-MORPHOLINE | 2-THIENYL |
| 83 | CH$_3$ | H | H | OCF$_3$ | H | — | 4-MORPHOLINE | 2-THIENYL |
| 84 | CH$_3$ | H | H | CF$_3$ | H | — | 4-MORPHOLINE | 2-THIENYL |
| 85 | CH$_3$ | H | H | SO$_2$CH$_3$ | H | — | 4-MORPHOLINE | 2-THIENYL |
| 86 | CH$_3$ | H | H | SO$_2$N(CH$_3$)$_2$ | H | — | 4-MORPHOLINE | 2-THIENYL |

TABLE 1-continued

| CPD | R¹ | R² | R³ | R⁴ | R⁷* | Z | Q₁ | Q₂ |
|---|---|---|---|---|---|---|---|---|
| 87 | $CH_3$ | H | H | H | H | — | 4-MORPHOLINE | 5-CHLORO-2-THIENYL |
| 88 | $CH_3$ | H | H | F | H | — | 4-MORPHOLINE | 5-CHLORO-2-THIENYL |
| 89 | $CH_3$ | H | H | Cl | H | — | 4-MORPHOLINE | 5-CHLORO-2-THIENYL |
| 90 | $CH_3$ | H | H | $OCH_3$ | H | — | 4-MORPHOLINE | 5-CHLORO-2-THIENYL |
| 91 | $CH_3$ | H | H | $OCF_3$ | H | — | 4-MORPHOLINE | 5-CHLORO-2-THIENYL |
| 92 | $CH_3$ | H | H | $CF_3$ | H | — | 4-MORPHOLINE | 5-CHLORO-2-THIENYL |
| 93 | $CH_3$ | H | H | $SO_2CH_3$ | H | — | 4-MORPHOLINE | 5-CHLORO-2-THIENYL |
| 94 | $CH_3$ | H | H | $SO_2N(CH_3)_2$ | H | — | 4-MORPHOLINE | 5-CHLORO-2-THIENYL |
| 95 | $CH_3$ | H | H | H | H | — | 4-MORPHOLINE | 3,4,5-TRICHLORO-2-THIENYL |
| 96 | $CH_3$ | H | H | F | H | — | 4-MORPHOLINE | 3,4,5-TRICHLORO-2-THIENYL |
| 97 | $CH_3$ | H | H | Cl | H | — | 4-MORPHOLINE | 3,4,5-TRICHLORO-2-THIENYL |
| 98 | $CH_3$ | H | H | $OCH_3$ | H | — | 4-MORPHOLINE | 3,4,5-TRICHLORO-2-THIENYL |
| 99 | $CH_3$ | H | H | $OCF_3$ | H | — | 4-MORPHOLINE | 3,4,5-TRICHLORO-2-THIENYL |
| 100 | $CH_3$ | H | H | $CF_3$ | H | — | 4-MORPHOLINE | 3,4,5-TRICHLORO-2-THIENYL |
| 101 | $CH_3$ | H | H | $SO_2CH_3$ | H | — | 4-MORPHOLINE | 3,4,5-TRICHLORO-2-THIENYL |
| 102 | $CH_3$ | H | H | $SO_2N(CH_3)_2$ | H | — | 4-MORPHOLINE | 3,4,5-TRICHLORO-2-THIENYL |
| 103 | $CH_3$ | H | H | H | H | — | 4-MORPHOLINE | 2-FURANYL |
| 104 | $CH_3$ | H | H | F | H | — | 4-MORPHOLINE | 2-FURANYL |
| 105 | $CH_3$ | H | H | Cl | H | — | 4-MORPHOLINE | 2-FURANYL |
| 106 | $CH_3$ | H | H | $OCH_3$ | H | — | 4-MORPHOLINE | 2-FURANYL |
| 107 | $CH_3$ | H | H | $OCF_3$ | H | — | 4-MORPHOLINE | 2-FURANYL |
| 108 | $CH_3$ | H | H | $CF_3$ | H | — | 4-MORPHOLINE | 2-FURANYL |
| 109 | $CH_3$ | H | H | $SO_2CH_3$ | H | — | 4-MORPHOLINE | 2-FURANYL |
| 110 | $CH_3$ | H | H | $SO_2N(CH_3)_2$ | H | — | 4-MORPHOLINE | 2-FURANYL |
| 111 | $CH_3$ | H | H | H | H | — | 4-MORPHOLINE | 5-CHLORO-2-FURANYL |
| 112 | $CH_3$ | H | H | F | H | — | 4-MORPHOLINE | 5-CHLORO-2-FURANYL |
| 113 | $CH_3$ | H | H | Cl | H | — | 4-MORPHOLINE | 5-CHLORO-2-FURANYL |
| 114 | $CH_3$ | H | H | $OCH_3$ | H | — | 4-MORPHOLINE | 5-CHLORO-2-FURANYL |
| 115 | $CH_3$ | H | H | $OCF_3$ | H | — | 4-MORPHOLINE | 5-CHLORO-2-FURANYL |
| 116 | $CH_3$ | H | H | $CF_3$ | H | — | 4-MORPHOLINE | 5-CHLORO-2-FURANYL |
| 117 | $CH_3$ | H | H | $SO_2CH_3$ | H | — | 4-MORPHOLINE | 5-CHLORO-2-FURANYL |
| 118 | $CH_3$ | H | H | $SO_2N(CH_3)_2$ | H | — | 4-MORPHOLINE | 5-CHLORO-2-FURANYL |
| 119 | $CH_3$ | H | H | H | H | — | 4-MORPHOLINE | 3-FURANYL |
| 120 | $CH_3$ | H | H | F | H | — | 4-MORPHOLINE | 3-FURANYL |
| 121 | $CH_3$ | H | H | Cl | H | — | 4-MORPHOLINE | 3-FURANYL |
| 122 | $CH_3$ | H | H | $OCH_3$ | H | — | 4-MORPHOLINE | 3-FURANYL |
| 123 | $CH_3$ | H | H | $OCF_3$ | H | — | 4-MORPHOLINE | 3-FURANYL |
| 124 | $CH_3$ | H | H | $CF_3$ | H | — | 4-MORPHOLINE | 3-FURANYL |
| 125 | $CH_3$ | H | H | $SO_2CH_3$ | H | — | 4-MORPHOLINE | 3-FURANYL |
| 126 | $CH_3$ | H | H | $SO_2N(CH_3)_2$ | H | — | 4-MORPHOLINE | 3-FURANYL |
| 127 | $CH_3$ | H | H | H | H | — | 4-MORPHOLINE | 3-THIENYL |
| 128 | $CH_3$ | H | H | F | H | — | 4-MORPHOLINE | 3-THIENYL |
| 129 | $CH_3$ | H | H | Cl | H | — | 4-MORPHOLINE | 3-THIENYL |
| 130 | $CH_3$ | H | H | $OCH_3$ | H | — | 4-MORPHOLINE | 3-THIENYL |
| 131 | $CH_3$ | H | H | $OCF_3$ | H | — | 4-MORPHOLINE | 3-THIENYL |
| 132 | $CH_3$ | H | H | $CF_3$ | H | — | 4-MORPHOLINE | 3-THIENYL |
| 133 | $CH_3$ | H | H | $SO_2CH_3$ | H | — | 4-MORPHOLINE | 3-THIENYL |
| 134 | $CH_3$ | H | H | $SO_2N(CH_3)_2$ | H | — | 4-MORPHOLINE | 3-THIENYL |
| 135 | $CH_3$ | H | H | H | H | — | 1-PIPERIDINYL | 2-CHLOROPHENYL |
| 136 | $CH_3$ | H | H | F | H | — | 1-PIPERIDINYL | 2-CHLOROPHENYL |
| 137 | $CH_3$ | H | H | Cl | H | — | 1-PIPERIDINYL | 2-CHLOROPHENYL |
| 138 | $CH_3$ | H | H | $OCH_3$ | H | — | 1-PIPERIDINYL | 2-CHLOROPHENYL |
| 139 | $CH_3$ | H | H | $OCF_3$ | H | — | 1-PIPERIDINYL | 2-CHLOROPHENYL |
| 140 | $CH_3$ | H | H | $CF_3$ | H | — | 1-PIPERIDINYL | 2-CHLOROPHENYL |
| 141 | $CH_3$ | H | H | $SO_2CH_3$ | H | — | 1-PIPERIDINYL | 2-CHLOROPHENYL |
| 142 | $CH_3$ | H | H | $SO_2N(CH_3)_2$ | H | — | 1-PIPERIDINYL | 2-CHLOROPHENYL |
| 143 | $CH_3$ | H | H | H | H | — | 1-PIPERIDINYL | 2,3-DICHLOROPHENYL |
| 144 | $CH_3$ | H | H | F | H | — | 1-PIPERIDINYL | 2,3-DICHLOROPHENYL |
| 145 | $CH_3$ | H | H | Cl | H | — | 1-PIPERIDINYL | 2,3-DICHLOROPHENYL |
| 146 | $CH_3$ | H | H | $OCH_3$ | H | — | 1-PIPERIDINYL | 2,3-DICHLOROPHENYL |
| 147 | $CH_3$ | H | H | $OCF_3$ | H | — | 1-PIPERIDINYL | 2,3-DICHLOROPHENYL |
| 148 | $CH_3$ | H | H | $CF_3$ | H | — | 1-PIPERIDINYL | 2,3-DICHLOROPHENYL |
| 149 | $CH_3$ | H | H | $SO_2CH_3$ | H | — | 1-PIPERIDINYL | 2,3-DICHLOROPHENYL |
| 150 | $CH_3$ | H | H | $SO_2N(CH_3)_2$ | H | — | 1-PIPERIDINYL | 2,3-DICHLOROPHENYL |
| 151 | $CH_3$ | H | H | H | H | — | 1-PIPERIDINYL | 1-NAPHTHYL |
| 152 | $CH_3$ | H | H | F | H | — | 1-PIPERIDINYL | 1-NAPHTHYL |
| 153 | $CH_3$ | H | H | Cl | H | — | 1-PIPERIDINYL | 1-NAPHTHYL |
| 154 | $CH_3$ | H | H | $OCH_3$ | H | — | 1-PIPERIDINYL | 1-NAPHTHYL |
| 155 | $CH_3$ | H | H | $OCF_3$ | H | — | 1-PIPERIDINYL | 1-NAPHTHYL |
| 156 | $CH_3$ | H | H | $CF_3$ | H | — | 1-PIPERIDINYL | 1-NAPHTHYL |
| 157 | $CH_3$ | H | H | $SO_2CH_3$ | H | — | 1-PIPERIDINYL | 1-NAPHTHYL |
| 158 | $CH_3$ | H | H | $SO_2N(CH_3)_2$ | H | — | 1-PIPERIDINYL | 1-NAPHTHYL |
| 159 | $CH_3$ | H | H | H | H | — | 1-PIPERIDINYL | 2-NAPHTHYL |
| 160 | $CH_3$ | H | H | F | H | — | 1-PIPERIDINYL | 2-NAPHTHYL |
| 161 | $CH_3$ | H | H | Cl | H | — | 1-PIPERIDINYL | 2-NAPHTHYL |
| 162 | $CH_3$ | H | H | $OCH_3$ | H | — | 1-PIPERIDINYL | 2-NAPHTHYL |
| 163 | $CH_3$ | H | H | $OCF_3$ | H | — | 1-PIPERIDINYL | 2-NAPHTHYL |

TABLE 1-continued

| CPD | R¹ | R² | R³ | R⁴ | R⁷* | Z | Q₁ | Q₂ |
|---|---|---|---|---|---|---|---|---|
| 164 | CH₃ | H | H | CF₃ | H | — | 1-PIPERIDINYL | 2-NAPHTHYL |
| 165 | CH₃ | H | H | SO₂CH₃ | H | — | 1-PIPERIDINYL | 2-NAPHTHYL |
| 166 | CH₃ | H | H | SO₂N(CH₃)₂ | H | — | 1-PIPERIDINYL | 2-NAPHTHYL |
| 167 | CH₃ | H | H | H | H | — | 1-PIPERIDINYL | 2-THIENYL |
| 168 | CH₃ | H | H | F | H | — | 1-PIPERIDINYL | 2-THIENYL |
| 169 | CH₃ | H | H | Cl | H | — | 1-PIPERIDINYL | 2-THIENYL |
| 170 | CH₃ | H | H | OCH₃ | H | — | 1-PIPERIDINYL | 2-THIENYL |
| 171 | CH₃ | H | H | OCF₃ | H | — | 1-PIPERIDINYL | 2-THIENYL |
| 172 | CH₃ | H | H | CF₃ | H | — | 1-PIPERIDINYL | 2-THIENYL |
| 173 | CH₃ | H | H | SO₂CH₃ | H | — | 1-PIPERIDINYL | 2-THIENYL |
| 174 | CH₃ | H | H | SO₂N(CH₃)₂ | H | — | 1-PIPERIDINYL | 2-THIENYL |
| 175 | CH₃ | H | H | H | H | — | 1-PIPERIDINYL | 5-CHLORO-2-THIENYL |
| 176 | CH₃ | H | H | F | H | — | 1-PIPERIDINYL | 5-CHLORO-2-THIENYL |
| 177 | CH₃ | H | H | Cl | H | — | 1-PIPERIDINYL | 5-CHLORO-2-THIENYL |
| 178 | CH₃ | H | H | OCH₃ | H | — | 1-PIPERIDINYL | 5-CHLORO-2-THIENYL |
| 179 | CH₃ | H | H | OCF₃ | H | — | 1-PIPERIDINYL | 5-CHLORO-2-THIENYL |
| 180 | CH₃ | H | H | CF₃ | H | — | 1-PIPERIDINYL | 5-CHLORO-2-THIENYL |
| 181 | CH₃ | H | H | SO₂CH₃ | H | — | 1-PIPERIDINYL | 5-CHLORO-2-THIENYL |
| 182 | CH₃ | H | H | SO₂N(CH₃)₂ | H | — | 1-PIPERIDINYL | 5-CHLORO-2-THIENYL |
| 183 | CH₃ | H | H | H | H | — | 1-PIPERIDINYL | 3,4,5-TRICHLORO-2-THIENYL |
| 184 | CH₃ | H | H | F | H | — | 1-PIPERIDINYL | 3,4,5-TRICHLORO-2-THIENYL |
| 185 | CH₃ | H | H | Cl | H | — | 1-PIPERIDINYL | 3,4,5-TRICHLORO-2-THIENYL |
| 186 | CH₃ | H | H | OCH₃ | H | — | 1-PIPERIDINYL | 3,4,5-TRICHLORO-2-THIENYL |
| 187 | CH₃ | H | H | OCF₃ | H | — | 1-PIPERIDINYL | 3,4,5-TRICHLORO-2-THIENYL |
| 188 | CH₃ | H | H | CF₃ | H | — | 1-PIPERIDINYL | 3,4,5-TRICHLORO-2-THIENYL |
| 189 | CH₃ | H | H | SO₂CH₃ | H | — | 1-PIPERIDINYL | 3,4,5-TRICHLORO-2-THIENYL |
| 190 | CH₃ | H | H | SO₂N(CH₃)₂ | H | — | 1-PIPERIDINYL | 3,4,5-TRICHLORO-2-THIENYL |
| 191 | CH₃ | H | H | H | H | — | 1-PIPERIDINYL | 2-FURANYL |
| 192 | CH₃ | H | H | F | H | — | 1-PIPERIDINYL | 2-FURANYL |
| 193 | CH₃ | H | H | Cl | H | — | 1-PIPERIDINYL | 2-FURANYL |
| 194 | CH₃ | H | H | OCH₃ | H | — | 1-PIPERIDINYL | 2-FURANYL |
| 195 | CH₃ | H | H | OCF₃ | H | — | 1-PIPERIDINYL | 2-FURANYL |
| 196 | CH₃ | H | H | CF₃ | H | — | 1-PIPERIDINYL | 2-FURANYL |
| 197 | CH₃ | H | H | SO₂CH₃ | H | — | 1-PIPERIDINYL | 2-FURANYL |
| 198 | CH₃ | H | H | SO₂N(CH₃)₂ | H | — | 1-PIPERIDINYL | 2-FURANYL |
| 199 | CH₃ | H | H | H | H | — | 1-PIPERIDINYL | 3-FURANYL |
| 200 | CH₃ | H | H | F | H | — | 1-PIPERIDINYL | 3-FURANYL |
| 201 | CH₃ | H | H | Cl | H | — | 1-PIPERIDINYL | 3-FURANYL |
| 202 | CH₃ | H | H | OCH₃ | H | — | 1-PIPERIDINYL | 3-FURANYL |
| 203 | CH₃ | H | H | OCF₃ | H | — | 1-PIPERIDINYL | 3-FURANYL |
| 204 | CH₃ | H | H | CF₃ | H | — | 1-PIPERIDINYL | 3-FURANYL |
| 205 | CH₃ | H | H | SO₂CH₃ | H | — | 1-PIPERIDINYL | 3-FURANYL |
| 206 | CH₃ | H | H | SO₂N(CH₃)₂ | H | — | 1-PIPERIDINYL | 3-FURANYL |
| 207 | CH₃ | H | H | H | H | — | 1-PIPERIDINYL | 5-CHLORO-2-FURANYL |
| 208 | CH₃ | H | H | F | H | — | 1-PIPERIDINYL | 5-CHLORO-2-FURANYL |
| 209 | CH₃ | H | H | Cl | H | — | 1-PIPERIDINYL | 5-CHLORO-2-FURANYL |
| 210 | CH₃ | H | H | OCH₃ | H | — | 1-PIPERIDINYL | 5-CHLORO-2-FURANYL |
| 211 | CH₃ | H | H | OCF₃ | H | — | 1-PIPERIDINYL | 5-CHLORO-2-FURANYL |
| 212 | CH₃ | H | H | CF₃ | H | — | 1-PIPERIDINYL | 5-CHLORO-2-FURANYL |
| 213 | CH₃ | H | H | SO₂CH₃ | H | — | 1-PIPERIDINYL | 5-CHLORO-2-FURANYL |
| 214 | CH₃ | H | H | SO₂N(CH₃)₂ | H | — | 1-PIPERIDINYL | 5-CHLORO-2-FURANYL |
| 215 | CH₃ | H | H | H | H | — | 1-PIPERIDINYL | 3-THIENYL |
| 216 | CH₃ | H | H | F | H | — | 1-PIPERIDINYL | 3-THIENYL |
| 217 | CH₃ | H | H | Cl | H | — | 1-PIPERIDINYL | 3-THIENYL |
| 218 | CH₃ | H | H | OCH₃ | H | — | 1-PIPERIDINYL | 3-THIENYL |
| 219 | CH₃ | H | H | OCF₃ | H | — | 1-PIPERIDINYL | 3-THIENYL |
| 220 | CH₃ | H | H | CF₃ | H | — | 1-PIPERIDINYL | 3-THIENYL |
| 221 | CH₃ | H | H | SO₂CH₃ | H | — | 1-PIPERIDINYL | 3-THIENYL |
| 222 | H | H | H | SO₂N(CH₃)₂ | H | — | 1-PIPERIDINYL | 3-THIENYL |
| 223 | H | H | H | Cl | H | — | (CH₃)₃N⁺ | 2-CHLOROPHENYL |
| 224 | H | H | H | OCH₃ | H | — | (CH₃)₃N⁺ | 2,3-DICHLOROPHENYL |
| 225 | H | H | H | Cl | H | — | 2-PYRIDINYL | 2-CHLOROPHENYL |
| 226 | H | H | H | OCH₃ | H | — | 2-PYRIDINYL | 2,3-DICHLOROPHENYL |
| 227 | H | H | H | Cl | H | — | 1-PYRROLIDINYL | 9-ANTHRACYL |
| 228 | H | H | H | OCH₃ | H | — | 1PYRROLIDINYL | 9-ANTHRACYL |
| 229 | H | H | H | Cl | H | — | 2-PYRIDINYL | 2-CHLOROPHENYL |
| 230 | H | H | H | OCH₃ | H | — | 2-PYRIDINYL | 2,3-DICHLOROPHENYL |
| 231 | H | H | H | Cl | H | — | 2-PYRROLIDINYL | 9-ANTHRACYL |
| 232 | H | H | H | OCH₃ | H | — | 2-PYRROLIDINYL | 9-ANTHRACYL |
| 233 | H | H | H | Cl | H | — | 1-PIPERAZINYL | 2-CHLOROPHENYL |
| 234 | H | H | H | OCH₃ | H | — | 2-PIPERAZINYL | 2,3-DICHLOROPHENYL |
| 235 | H | H | H | Cl | H | — | PHENYL | 9-ANTHRACYL |
| 236 | CH₃ | H | H | OCH₃ | H | — | PHENYL | 2-CHLOROPHENYL |
| 237 | CH₃ | H | H | Cl | H | — | PHENYL | 2,3-DICHLOROPHENYL |
| 238 | CH₃ | H | H | OCH₃ | H | — | 2-CHLOROPHENYL | 9-ANTHRACYL |
| 239 | CH₃ | H | H | Cl | H | — | 2,3-DICHLOROPHENYL | 2-CHLOROPHENYL |
| 240 | CH₃ | H | H | OCH₃ | H | — | 2-THIENYL | 2,3-DICHLOROPHENYL |

TABLE 1-continued

| CPD | R¹ | R² | R³ | R⁴ | R⁷* | Z | Q₁ | Q₂ |
|---|---|---|---|---|---|---|---|---|
| 241 | CH₃ | H | H | Cl | H | — | 3-THIENYL | 2-CHLOROPHENYL |
| 242 | CH₃ | H | H | OCH₃ | H | CO | 1-PIPERIDINYL | 2-CHLOROPHENYL |
| 243 | CH₃ | H | H | Cl | H | CO | 1-PIPERIDINYL | 2,3-DICHLOROPHENYL |
| 244 | CH₃ | H | H | OCH₃ | H | CO | 1-PIPERIDINYL | 9-ANTHRACYL |
| 245 | CH₃ | H | H | Cl | H | CO | 1-PIPERIDINYL | 2-THIENYL |
| 246 | CH₃ | H | H | OCH₃ | H | CO | 1-PIPERIDINYL | 3-THIENYL |
| 247 | CH₃ | H | H | Cl | H | CO | 1-PIPERIDINYL | 2-FURANYL |
| 248 | CH₃ | H | H | OCH₃ | H | CO | 1-PIPERIDINYL | 3-FURANYL |
| 249 | CH₃ | H | H | Cl | H | CO | 1-PIPERIDINYL | 1-NAPHTHYL |
| 250 | CH₃ | H | H | OCH₃ | H | CO | 1-PIPERIDINYL | 2-NAPHTHYL |
| 251 | CH₃ | H | H | Cl | H | CO | 1-PYRROLIDINYL | 2-CHLOROPHENYL |
| 252 | CH₃ | H | H | OCH₃ | H | CO | 1-PYRROLIDINYL | 2,3-DICHLOROPHENYL |
| 253 | CH₃ | H | H | Cl | H | CO | 1-PYRROLIDINYL | 9-ANTHRACYL |
| 254 | CH₃ | H | H | OCH₃ | H | CO | 1-PYRROLIDINYL | 2-THIENYL |
| 255 | CH₃ | H | H | Cl | H | CO | 1-PYRROLIDINYL | 3-THIENYL |
| 256 | CH₃ | H | H | OCH₃ | H | CO | 1-PYRROLIDINYL | 2-FURANYL |
| 257 | CH₃ | H | H | H | H | CO | 4-MORPHOLINE | 1-NAPHTHYL |
| 258 | CH₃ | H | H | OCH₃ | H | CO | 4-MORPHOLINE | 2,5-DICHLOROPHENYL |
| 259 | CH₃ | H | H | OCH₃ | H | CO | 4-MORPHOLINE | 2,3-DICHLOROPHENYL |
| 260 | CH₃ | H | H | OCH₃ | H | CO | 4-MORPHOLINE | 2-CHLORO-4FLUOROPHENYL |
| 261 | CH₃ | H | H | OCH₃ | H | CO | 4-MORPHOLINE | 3-CHLOROPHENYL |
| 262 | CH₃ | H | H | H | H | — | COOCH₃ | 1-NAPHTHYL |
| 263 | CH₃ | H | H | H | H(m = 2) | — | 4-MORPHOLINE | 1-NAPHTHYL |
| 264 | CH₃ | H | H | OCH₃ | H(m = 2) | — | 4-MORPHOLINE | 2,3-DICHLOROPHENYL |
| 265 | CH₃ | H | H | H | H | — | 4-MORPHOLINE | 2-CHLOROPHENYL |
| 266 | CH₃ | H | H | OCH₃ | H(m = 2) | — | 4-MORPHOLINE | 1-NAPHTHYL |
| 267 | CH₃ | H | H | OCH₃ | H(m = 2) | — | 4-MORPHOLINE | 2-CHLOROPHENYL |
| 268 | CH₃ | H | H | H | H(m = 2) | — | 4-MORPHOLINE | 2-CHLOROPHENYL |

*m = 1 EXCEPT NOTED OTHERWISE

TABLE 2

ELEMENTAL ANALYSIS

| | | CALCULATED | | | FOUND | | |
|---|---|---|---|---|---|---|---|
| CPD | FORMULA | C | H | N | C | H | N |
| 31 | $C_{23}H_{23}ClN_2O_4$ | 64.71 | 5.43 | 6.56 | 64.78 | 5.69 | 6.42 |
| 63 | $C_{25}H_{23}ClN_2O_2$ | 71.33 | 5.99 | 6.65 | 71.23 | 6.99 | 6.57 |
| 258 | $C_{23}H_{22}Cl_2N_2O_4$ | 59.88 | 4.81 | 6.07 | 59.56 | 4.86 | 6.09 |
| 259 | $C_{23}H_{22}Cl_2N_2O_4$ | 59.88 | 4.81 | 6.07 | 59.25 | 4.89 | 5.81 |
| 260 | $C_{23}H_{22}ClFN_2O_4$ | 62.09 | 4.98 | 6.30 | 62.05 | 5.04 | 6.53 |
| 261 | $C_{23}H_{23}ClN_2O_4$ | 64.71 | 5.43 | 6.56 | 63.36 | 5.29 | 6.47 |
| 263 | $C_{26}H_{27}ClN_2O_2$ | 71.80 | 6.26 | 6.44 | 71.64 | 6.36 | 6.15 |

The preferred compounds are realized when:

$R^1$ is H, lower alkyl, or lower fluorinated alkyl;

$R^{2-4}$ is independently H, lower alkyl, $OR^1$, halogen, or lower fluorinated alkyl;

$R^7$ is H, or lower alkyl; and $Q_1$ is morpholine, piperazine, piperidine, or pyrrolidine.

The most preferred compounds are realized when:

$R^1$ is lower alkyl;

$R^{2-4}$ is independently is H, or $OR^1$;

$R_7$ is H;

$Q_1$ is morpholine;

m is 2; and

Z is a bond.

Specific compounds are:

2-[1-(2-Chlorobenzoyl)-5-methoxy-2-methyl-1H-indol-3-yl]-1-[morpholin-4-yl]ethanone;

2-Methyl-3-(morpholin-4-yl)methyl-1-(1-naphthoyl)-1H-indole;

2-Methyl-1-(1-naphthoyl)-1H-indol-3-ylacetic acid, methyl ester;

1-(2-Chlorobenzoyl)-5-methoxy-2-methyl-3-(morpholin-4-ylmethyl)-1H-indole;

1-(2,3-Dichlorobenzoyl)-2-methyl-3-(morpholin-4-ylmethyl)-1H-indole;

1-(2,3-Dichlorobenzoyl)-5-methoxy-2-methyl-3-(morpholin-4-ylmethyl)-1H-indole;

1-(1-Naphthoyl)-5-methoxy-2-methyl-3-(morpholin-4-ylmethyl)-1H-indole;

1-(2,3-Dichlorobenzoyl)-5-methoxy-2-methyl-3-(2-(morpholin-4-yl)ethyl)-1H-indole;

1-(2-Chlorobenzoyl)-2-methyl-3-(morpholin-4-ylmethyl)-1H-indole;

1-(1-Naphthoyl)-5-Methoxy-2-methyl-3-(2-(morpholin-4-yl)ethyl)-1H-indole;

1-(2-Chlorobenzoyl)-5-methoxy-2-methyl-3-(2-(morpholin-4-yl)ethyl)-1H-indole; and 1-(2-Chlorobenzoyl)-2-methyl-3-(2-(morpholin-4-yl)ethyl)-1H-indole.

Utilities

The ability of the compounds of formula I to mimic the actions of the cannabinoids makes them useful for preventing or reversing the symptoms that can be treated with cannabis, some of its derivatives and synthetic cannabinoids in a human subject. Thus, compounds of formula I are useful to treat, prevent, or ameliorate in mammals and especially in humans:

1—various ocular disorders such as glaucoma.

2—pulmonary disorders including diseases such as asthma, chronic bronchitis and related airway diseases.

3—allergies and allergic reactions such as allergic rhinitis, contact dermatitis, allergic conjunctivitis and the like.

4—inflammation such as arthritis or inflammatory bowel disease.

5—pain.

6—disorders of the immune system such as lupus, AIDS, etc.

7—allograft rejection.

8—central nervous system diseases such as Tourette's syndrome, Parkinson's disease, Huntingdon's disease, epilepsy, various psychotic afflictions such as depression, manic depression, etc.

9—vomiting, and nausea and vertigo, especially in the case of chemotherapy patients.

Dose Ranges

The magnitude of therapeutic dose of a compound of Formula I will, of course, vary with the nature of the severity of the condition to be treated and with the particular compound of Formula I and its route of administration and vary upon the clinician's judgment. It will also vary according to the age, weight and response of the individual patient. An effective dosage amount of the active component can thus be determined by the clinician after a consideration of all the criteria and using is best judgment on the patient's behalf.

An ophthalmic preparation for ocular administration comprising 0.001–1% by weight solutions or suspensions of the compounds of Formula I in an acceptable ophthalmic formulation may be used.

Pharmaceutical Compositions

Any suitable route of administration may be employed for providing a mammal, especially a human with an effective dosage of a compound of the present invention. For example, oral, parenteral and topical may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carder and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, parenteral and ocular (ophthalmic). They may be conveniently presented in unit dosage form and prepared by any of the methods well-known in the art of pharmacy.

In practical use, the compounds of Formula I can be combined as the active ingredient in intimate admixture with a pharmaceutical carder according to conventional pharmaceutical compounding techniques. The carder may take a wide variety of forms depending on the form of preparation desired for administration. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carders such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carders are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Combinations with Other Drugs

In addition to the compounds of Formula I, the pharmaceutical compositions of the present invention can also contain other active ingredients or prodrugs thereof. These other active species may be beta-blockers such as timolol, topical carbonic anhydrase inhibitors such as Dorzolamide, systemic carbonic anhydrase inhibitors such as acetolamide, cholinergic agents such as pilocarpine and its derivatives, prostaglandin F receptor agonists such as Latanoprost, ajmaline and its derivatives, $b_2$ adrenergic agonists such as epinephrine, glutamate antagonists, aminosteroids, diuretics, and any other compound used alone or in combination in the treatment of glaucoma. The weight ratio of the compound of the Formula I to the second active ingredient may be varied and will depend upon the effective dose of each ingredient. Generally, an effective dose of each will be used. Thus, for example, when a compound of the Formula I is combined with a b-blockers, a carbonic anhydrase inhibitor, a pilocarpine derivative or a prostaglandin agonist, the weight ratio of the compound of the Formula I to the other drug will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis

Compounds of the present invention can be prepared according to the following non-limiting methods. Temperatures are in degrees Celsius.

Method A

The starting indoles used are either commercially available or prepared from an appropiate hydrazine II and a properly substituted aldehyde or ketone III as described in U.S. Pat. No. 3,161,654 (incorporated herein). The indole IV obtained is then treated with an acyl chloride or bromide of a properly substituted $Q_2$ and a base to afford the desired indole I. When $Z-Q^1$ is an ester, it can be hydrolysed to the desired acid Ia with a base such as 1N NaOH in a protic solvent such as MeOH—$H_2O$.

METHOD A

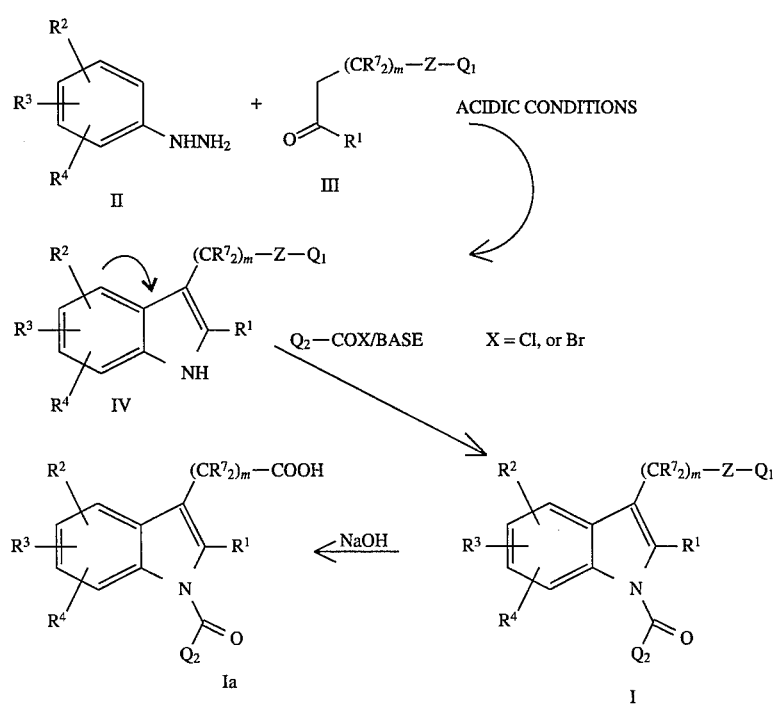

Method B

The acids Ia can be converted to a variety of esters Ib by dissolution in the appropriate lower alkyl alcohol with a strong acid such as 10% $H_2SO_4$ and heated between 60°–90° C. for 3–12 h (Fischer conditions).

METHOD B

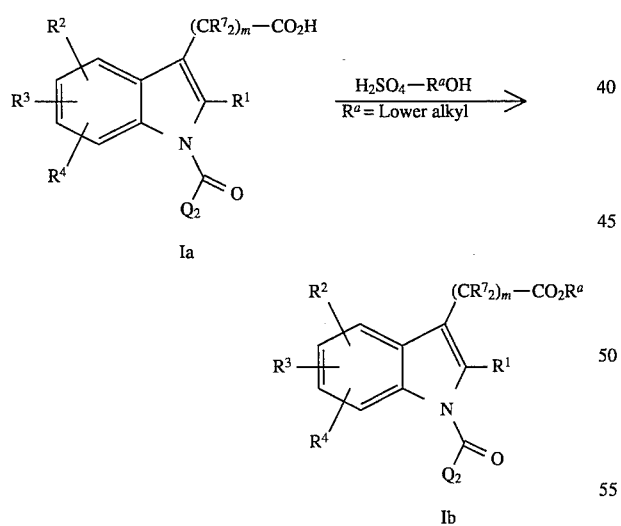

Method C

Acids Ia are treated with a chlorinating agent such as oxalyl chloride in an inert solvent (methylene chloride, dichloroethane, etc.). The resulting acyl halide is then treated with amines or thiols in the presence of a base (excess amine, $Et_3N$, etc.) to afford the corresponding amide Ic or thiol ester Id.

METHOD C

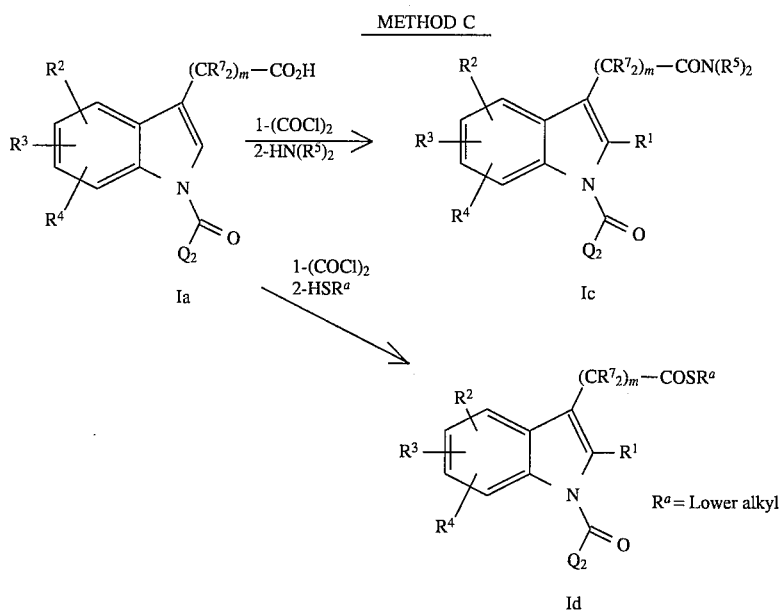

Method D

The primary amides of Ic in an inert solvent such as THF, Et$_2$O, etc. and a base such as pyridine are treated with a dehydrating agent such as trifluoroacetic anhydride at 0° C. to afford the nitrile Ie.

Method E

Acids Ia are treated with borane according to the literature (J. Org. Chem. 1973, 38, 2786) to afford the alcohols If.

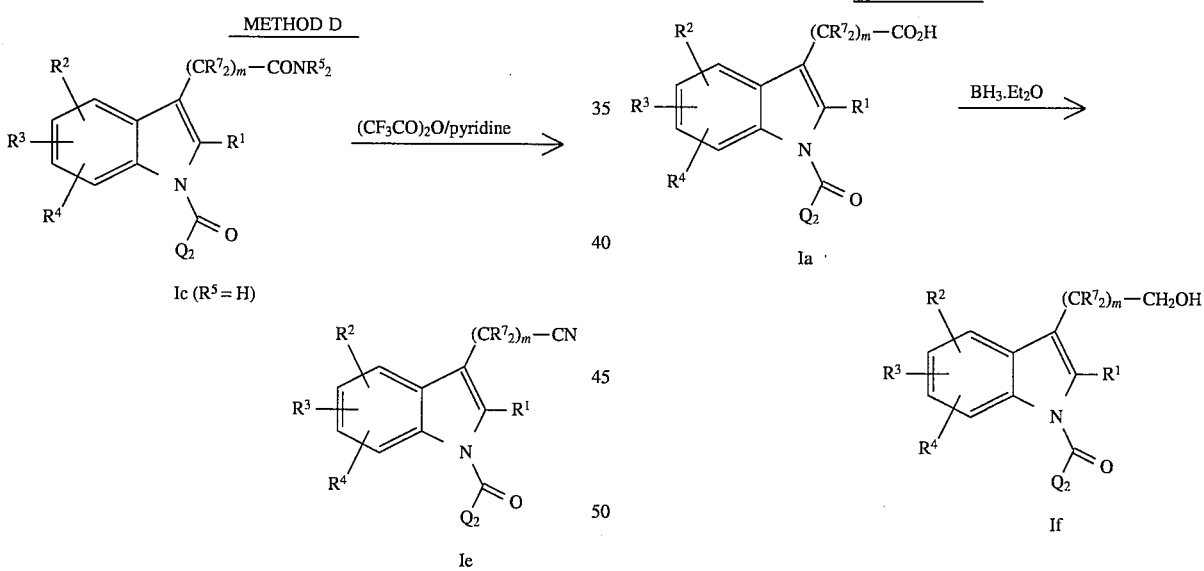

Method F

Compounds of type If can be converted to their mesylate or tosylate in an inert solvent such as CH$_2$Cl$_2$ in the presence of a base such as Et$_3$N and then reacted with various nucleophiles such as alcohols, thiols and amines to produce compounds Ig, Ih and Ii.

METHOD F

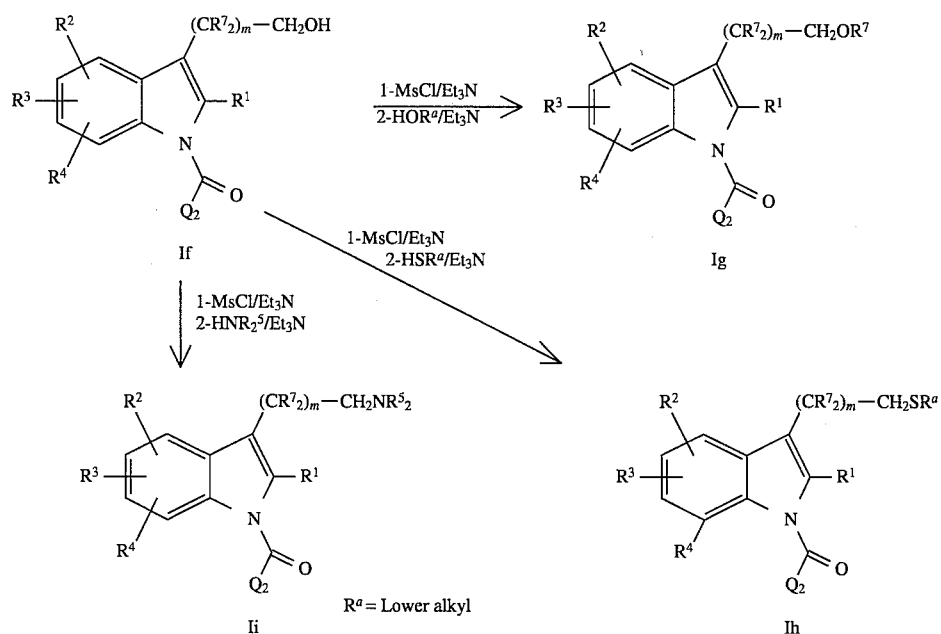

Method G

When compounds of type If are subjected to Swern oxidation (J. Org. Chem. 1978, 43, 2480), with PCC (Tetrahedron Lett. 1975, 2647) or other oxidizing agents, aldehyde Ij is obtained.

METHOD G

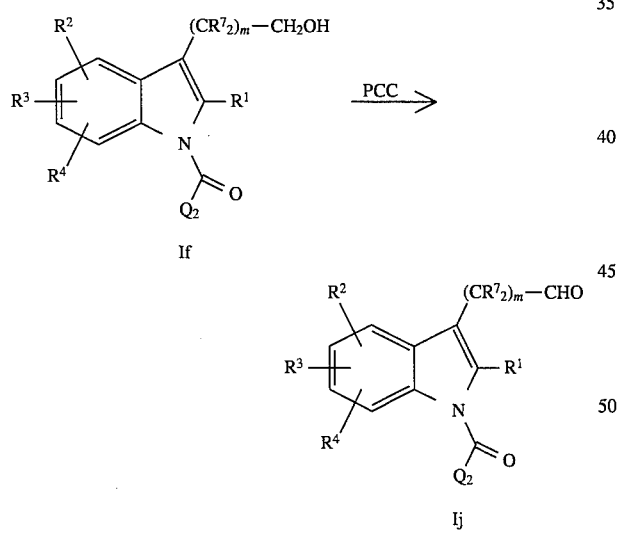

Method H

Compounds of type Ih can be reduced to the alkyl chain by reaction with Raney-Nickel in a protic solvent such as ethanol to afford Ik, which can also be prepared by a Fischer indole synthesis starting with an appropriate hydrazine II and a ketone or aldehyde IIIa under acidic conditions. Compound Ih can be oxidized to the sulfoxide or sulfone using for example $H_2O_2$ or MCPBA to give Il.

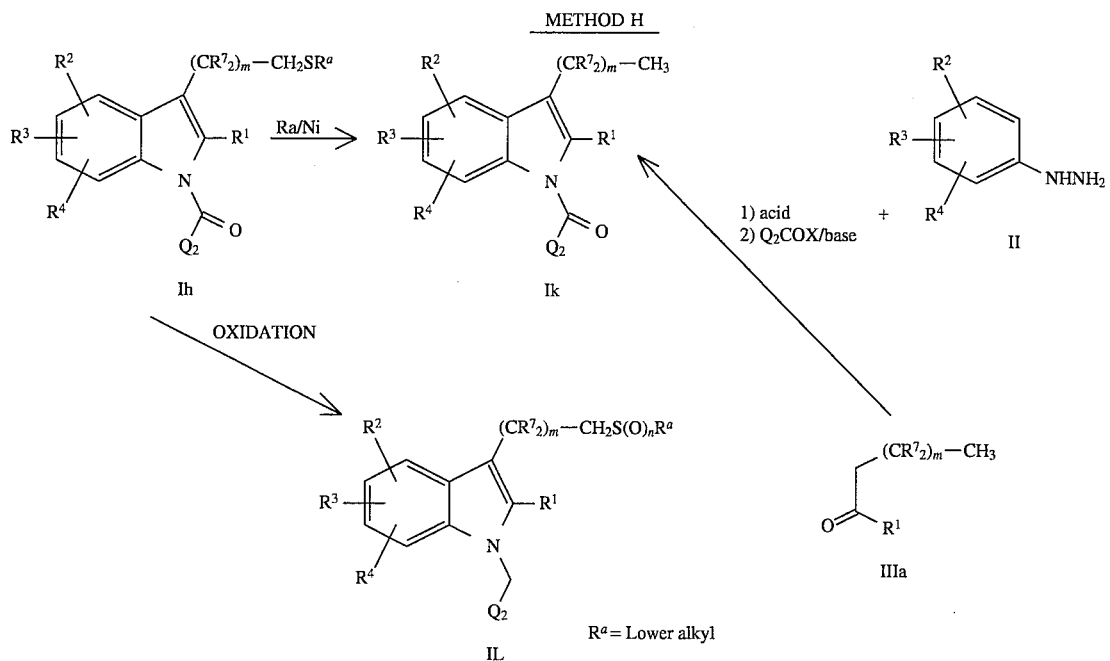

Method I

An indole of type V can be deprotonated with a strong base such as MeMgBr, treated with $ZnCl_2$ to exchange the metal when necessary, and an alkylating agent or (other electrophile) added to the mixture to yield compound of type IVa. This in turn according to method A can be converted to a compound of type I.

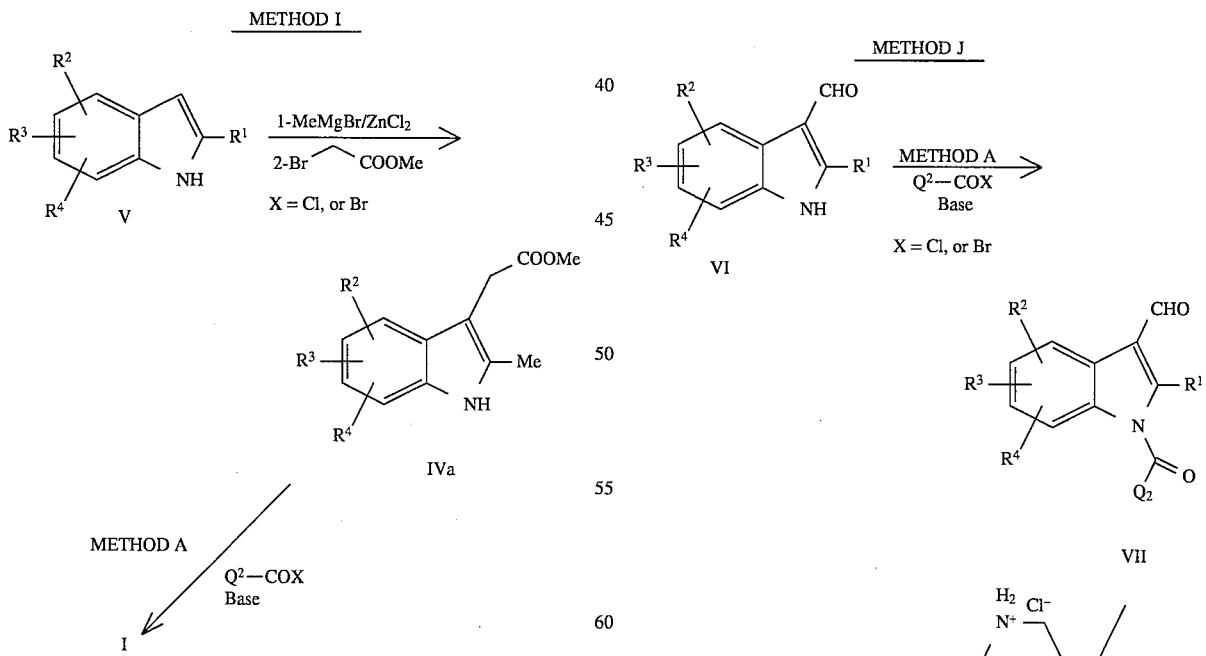

Method J

An indole of type VI can be treated according to method A to yield VII which can be converted to Im with an amine in presence of a reducing agent such as $NaBH_3CN$.

-continued
METHOD J

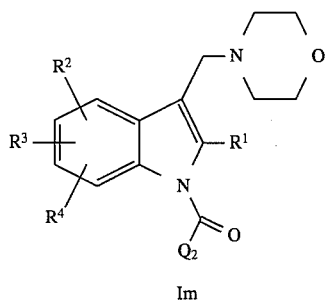

Im

Method K

A carboxylic acidic of type VIII can be coupled with various amines in an inert solvent such as $CH_2Cl_2$ using DCC or the like to yield IX, which can then be converted to In according to method A.

METHOD K

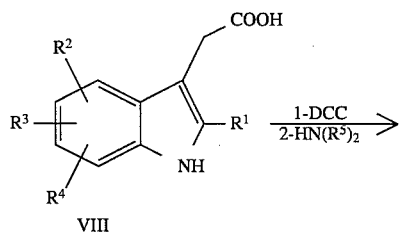

VIII

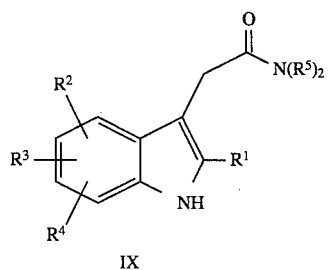

IX

METHOD A $\quad Q^2-COX$
Base

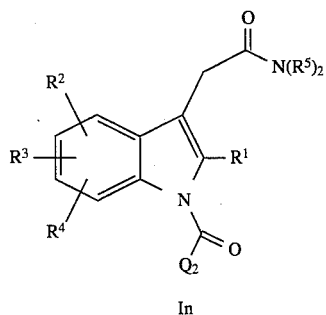

In

The invention will now be illustrated by the following non-limiting examples (Note: The examples in Table 1, above, that are not illustrated can be made by substantially similar procedures as discussed below) in which, unless stated otherwise:

(i) all operations are carried out at room or ambient temperature, that is, at a temperature in the range 18°–25° C.;

(ii) evaporation of solvent is carried out using a rotary evaporator under reduced pressure (600–4000 pascals: 4.5–30 mm Hg) with a bath temperature of up to 60° C.;

(iii) the course of reactions is followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products are assured by at least one of the following techniques: TLC, mass spectrometry, nuclear magnetic resonance (NMR) spectrometry, or microanalytical data;

(vi) yields are given for illustration only;

(vii) when given, NMR data are in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used: v (volume), w (weight), b.p. (boiling point), m.p. (melting point), L (liter(s)), mL (milliliters), g (gram(s)), mg (milligram(s)), mol (moles), mmol (millimoles), eq. (equivalent(s)).

EXAMPLES

Examples provided are intended to assist in a further understanding of the invention. Particular materials employed, species and conditions are intended to be further illustrative of the invention and not limitative of the reasonable scope thereof.

Example 1

2-[1-(2-Chlorobenzoyl)-5-methoxy-2-methyl-1H-indol-3-yl]-1[morpholin-4-yl]ethanone Step 1: 2-[5-methoxy-2-methyl-1H-indol-3-yl]-1-[morpholin-4-yl]ethanone To 5-methoxy-2-methyl-3-indoleacetic acid (0.665g; 3.03 mmol) in 6 mL of THF was added DCC (0.661 g; 3.2 mmol). After 2 h of stirring, morpholine (1 mL; 11.4 mmol) was added and stirred for another 1 h. The reaction mixture was filtered and the solvent removed. Chromatography on silica gel (eluted with EtOAc) yielded 0.585 g (64%) of the title compound.

$^1$H NMR (CDCl$_3$, 400 MHz) $\delta$2.30 (s, 3H), 3.38 (m, 4H), 3.60 (m, 4H), 3.70 (s, 2H), 3.82 (s, 3H), 6.7 (m, 1H), 6.93 (s, 1H), 7.09 (d, 1H) and 7.97 (s, 1H).

Step 2: 2-[1-(2-Chlorobenzoyl)-5-methoxy-2-methyl-1H-indol-3-yl]- 1-[morpholin-4-yl]ethanone To the amide (0.506 g; 1.75 mmol) from step 1 in 10 mL of THF and 0.9 mL of HMPA cooled to −78° C. was added KHMDS 0.5M (3.5 mL; 1.75 mmol) dropwise. The temperature was raised to −22° C. for 30 min and brought back to −78° C. Then 2-chlorobenzoyl chloride (0.33 mL; 2.61 mmol) was added and left stirring for 16 hr. It was then poured into cold water-EtOAc (50 mL). The organic phase was washed with H$_2$O (2×15 mL) and brine. The organic phase was dried over Na$_2$SO$_4$ and the solvent removed. Chromatography on silica gel (eluted with EtOAc) followed by a swish in CH$_2$Cl$_2$ (hot)—hexane afforded 0.462 g (78%) of the title compound.

$^1$H NMR (CDCl$_3$, 400 MHz) δ2.22 (s, 3H), 3.44 (m, 4H), 3.61 (s, 4H), 3.66 (s, 2H), 3.80 (s, 3H), 6.67–6.70 (dd, 1H), 6.96 (d, 1H), 7.10 (d, 1H), and 7.39–7.50 (m, 4H).

Example 2

2-Methyl-3-(morpholin-4-yl)methyl-1-(1-naphthoyl)-1H-indole

Step 1: 3-Formyl-2-methyl-1-(1-naphthoyl)-1H-indole

To 3-formyl-2-methylindole (4.30 g; 27.0 mmol) in 70 mL of DMF at r.t. was added NaH 80% (0.861 mg). After 30 min of stirring the solution was cooled to 0° C. and a solution of 1-naphthoyl chloride (5.04 g, 29.3 mmol) in 10 mL of DMF was added dropwise. The mixture was left stirring for 16 h at r.t. and poured into cold water-EtOAc (100mL). The organic phase was washed with H$_2$O (2×25 mL) and brine. The organic phase was dried over Na$_2$SO$_4$ and the solvent removed. Chromatography on silica gel (eluted with 10% EtOAc in toluene) yielded 1.70 g (20%) of the title compound.

$^1$H NMR (CDCl$_3$, 400 MHz) δ2.64 (s, 3H), 6.95 (d, 1H), 7.04 (t, 1H), 7.10–7.30 (m, 1H), 7.51 (m, 1H), 7.59 (m, 3H), 7.96 (m, 1H), 8.11 (d, 1H) and 10.34 (s, 1H).

Step 2: 2-Methyl-3-(morpholin-4-yl)methyl-1-(1naphthoyl)-1H-indole

To the aldehyde (0.118 g; 0.38 mmol) from step 1 and morpholine hydrochloride (0.99 g; 3.8 mmol) in 10 mL of MeOH was added NaBH$_3$CN (0.057 g; 0.91 mmol) and the mixture was left stirring for 16 h at r.t. Another 60 mg of NaBH$_3$CN was added and left stirring 8 h. The reaction was then poured into H$_2$O-EtOAc (20 mL–50 mL) and saturated with NaCl. The organic extracts were washed with brine and dry over Na$_2$SO$_4$. The solvent was removed and the crude product purified by chromatography on silica gel (eluted with 10%→30% EtOAc in toluene) to yield 0.99 g (68%) of the title compound.

$^1$H NMR (CDCl$_3$, 400 MHz) δ2.18 (s, 3H), 2.46 (m, 4H), 3.59 (s, 2H), 3.67 (m, 4H). 7.02 (t, 1H), 7.20 (m, 3H), 7.40–7.55 (m,2H) and 8.04 (d, 1H).

Example 3

2-Methyl-1-(1-naphthoyl)-1H-indol-3-ylacetic acid, methyl ester

Step 1: 2-Methyl-1H-indol-3-ylacetic acid, methyl ester.

To 2-methyl indole (1.69 g; 12.9 mmol) in 10 mL of THF at 0° C. was added MeMgBr 1.4M (12.9 mmol). After 30 min at 0° C. ZnCl$_2$ 1M (12.9 mL; 12.9 mmol) in THF was added and the reaction stirred for an other 30 min at r.t. Methyl bromoacetate (1.4 mL; 14.7 mmol) was added dropwise and left stirring for 48 h. The mixture was poured into aqueous NaHCO$_3$, extracted with EtOAc (3×25 mL) and the combined organic extracts were washed with brine. The solution was dried over Na$_2$SO$_4$ and the solvent removed. Chromatography on silica gel (eluted with 5% EtOAc in hexane) yielded 1.13g (43%) of the title compound.

$^1$H NMR (CDCl$_3$, 400 MHz) δ5 2.39 (s, 3H), 3.64 (s, 3H), 3.68 (s, 2H), 7.05–7.13 (m, 2H), 7.22–7.26 (m, 1H), 7.49–7.52 (m, 1H) and 7.82 (s, Step 2: 2-Methyl-1-(1-naphthoyl)-1H-indol-3-ylacetic acid, methyl ester The compound of step 1 (1.13g; 5.56 mmol) in 6 mL of DMF was treated with NaH 80% (0.18 g; 5.99 mmol) at 25° C. After 30 min a solution of 1-naphthoyl chloride in 5 mL of DMF was added dropwise The reaction mixture was left stirring for 16 h and poured into cold water-EtOAc. The organic phase was washed with H$_2$O (2×15 mL) and brine, dried over Na$_2$SO$_4$ and the solvent removed. Chromatography on silica gel (eluted with 2% EtOAc in toluene) yielded 0.86 g (43%) of the title compound. $^1$H NMR (CDCL$_3$, 400 MHZ) Δ2.20 (S, 3H), 3.67 (S, 3H), 7.0 (M, 1H), 7.10–7.26 (M, 3H), 7.45–7.60 (M, 5H), 7.95 (M, 1H) AND 8.07 (M, 3H).

High Resolution Mass Spectra results were: Formula (C$_{23}$H$_{19}$NO$_3$+H$^+$); Calculated (358.14415); Found (358.14432)

EXAMPLE 4

1-(2,3-Dichlorobenzoyl)-5-methoxy-2-methyl-3-(2-(morpholin-4-yl)ethyl)-1H-indole Step 1: 5-Methoxy-2-methyl-3-(2-(morpholin-4-yl)ethyl)-1H-indole To 5-methoxy-2-methyl-1H-indole (5.00 g; 31.0 mmol) in 30 mL of dry THF at 0° C. was added dropwise MeMgBr (3.0M in Et$_2$O; 11.4 mL; 34.2 mmol). The solution was stirred 30 min at r.t. after which ZnCl$_2$ (0.5M in THF; 64 mL; 32 mmol) was added. The mixture was stirred at r.t., after 1 h, N-(2-iodoethyl)morpholine (14.41 g; 51.5 mmol) was added. The final mixture was stirred at r.t. overnight. The mixture was poored in saturated NaHCO$_3$ (100 mL), extracted with EtOAc (2×100 mL). The organic phase was washed with brine (100 mL), dried over Na$_2$SO$_4$, filtered, concentrated and flash chromatographed (Silica gel; EtOAc/Ace O to 10%) to yield 587 mg (7%) of the title compound.

$^{NMR\ (CDCl}$$_3$, 400MHz) δ5 2.36 (s, 3H), 2.64 (bs, 6H), 2.92 (bs, 2H), 3.83 (bd, 4H), 3.85 (s, 3H), 6.76 (dd, 1H), 6.97 (d, 1H), 7.15 (d, 2H), 7.68 (bs, NH).

Step 2: 1-(2,3,-Dichlorobenzoyl)-5-methoxy-2-methyl-3-(2-(morpholin-4-yl)ethyl)-1 H-indole To 5-methoxy-2-methyl-3-(2-(morpholin-4-yl)ethyl)-1H-indole (311 mg; 1.13 mmol) in 10 mL dry THF at −78° C. was added HMPA (590 μL; 3.39 mmol), then dropwise KHMDS (0.5M in Tol; 2.5 mL; 1.25 mmol). The solution was stirred 30 min at −22° C. then cooled to −78° C. after which 2,3-dichlorobenzoyl chloride (361 mg; 1.72 mmol) was added. The final mixture was allowed to reach r.t. slowly then stirred 1 h. The mixture was poored in saturated NaHCO$_3$ (25 mL), extracted with EtOAc (2×50 mL). The organic phase was washed with brine (50 mL), dried over Na$_2$SO$_4$, filtered, concentrated and flash chromatographed (Silica gel; EtOAc) to yield 503 mg (99%) of the title compound.

$^1$NMR (CDCl$_3$, 400 MHz) δ2.12 (s, 3H), 2.52 (m, 6H), 2.79 (t, 2H), 3.74 (t, 4H), 3.82 (s, 3H), 6.71 (dd, 1H), 6.91 (d, 1H), 7.34 (m, 3H), 7.61 (dd, 1H).

Elemental analysis for C$_{23}$H$_{24}$Cl$_2$N$_2$O$_3$.HCl, calcd: C: 57.1, H: 5.21, N: 5.79; found: C: 57.18, H: 5.26, N: 5.70.

what is claimed is:

1. A compound of the structural formula I:

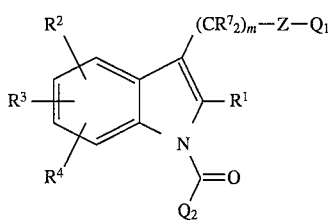

pharmaceutically acceptable salts thereof, or diastereomers, or enantiomers or mixtures thereof, wherein:

$R^1$ is H, lower alkyl, aryl, benzyl, or lower flourinated alkyl;

$R^{2-4}$ is independently, H, lower alkyl, lower fluorinated alkyl, halogen, $NO_2$, CN, $-(CR^7{}_2)_m-OR^1$, $-(CR^7{}_2)_m-S(O)_nR^6$, or $-(CR^7{}_2)_m-R^6$;

$R^5$ is H, lower alkyl, aryl, or benzyl;

$R^6$ is lower alkyl, aryl, benzyl, or $N(R^5)_2$;

$R^7$ is H, or lower alkyl;

$R^8$ is $R^7$, lower fluorinated alkyl, halogen, $OR^7$, or lower alkyl thio;

$Q_1$ is $N(R^7)_2$, wherein two $R^7$ groups may be joined to form a pyrrolidine, piperidine, piperazine, morpholine or thiomorpholine ring and their quaternary methyl ammonium salts;

$Q_2$ is naphthyl,

Z is a bond, m is 1–6; and n is 0,1, or 2.

2. The compounds of claim 1, wherein, $R^1$ is H, lower alkyl, or lower fluorinated alkyl;

$R^{2-4}$ is independently H, lower alkyl, $OR^1$, halogen, or lower fluorinated alkyl;

$R_7$ is H, or lower alkyl; and $Q_1$ is morpholine, piperazine, piperidine, or pyrrolidine.

3. The compounds of claim 1, wherein $R^1$ is lower alkyl;

$R^{2-4}$ is independently is H, or $OR^1$;

$R^7$ is H;

$Q_1$ is morpholine;

m is 2; and

Z is a bond.

4. The compounds of claim 1 which are:

2-Methyl-3-(morpholin-4-yl)methyl-1-(1-naphthoyl)-1H-indole;

1-(1-Naphthoyl)-5-methoxy-2-methyl-3-(morpholin-4-ylmethyl)-1H-indole; or 1-(1-Naphthoyl)-5-Methoxy-2-methyl-3-(2-(morpholin-4-yl)ethyl)-1H-indole.

5. A composition useful for treating ocular hypertension and glaucoma in a mammal, including humans, in need thereof, which comprises a pharmacologically effective amount of a cannabimimetic pharmacological agent of claim 1, known to be selective for CB2 receptors, in a carrier or diluent buffered to a pH suitable for ocular administration.

* * * * *

UNITED STATES PATENT AND TRADEMARK OFFICE
CERTIFICATE OF CORRECTION

PATENT NO. : 5,532,237
DATED : JUL. 2, 1996
INVENTOR(S): Michel Gallant, Yves Gareau, Daniel Guay, Marc Labelle
Petpiboon Prasit It is certified that the following error by the USPTO appears in the above-identified patent and that said Letters Patent is hereby corrected as shown below:

Col. 30, line 17, Claim 4, insert
-- 2-methyl-1-(1-naphthoyl)-1H-indol-3-ylacetic acid, methyl ester; --.

Signed and Sealed this

Eleventh Day of March, 1997

*Attest:*

BRUCE LEHMAN

*Attesting Officer*     *Commissioner of Patents and Trademarks*